(12) United States Patent
Boccara et al.

(10) Patent No.: US 9,255,785 B2
(45) Date of Patent: Feb. 9, 2016

(54) METHOD AND DEVICE FOR HIGH RESOLUTION FULL FIELD INTERFERENCE MICROSCOPY

(75) Inventors: Albert Claude Boccara, Paris (FR); Fabrice Harms, Orsay (FR); Bertrand Le Conte Chrestien De Poly, Paris (FR)

(73) Assignee: LLTECH MANAGEMENT, Paris (FR)

( * ) Notice: Subject to any disclaimer, the term of this patent is extended or adjusted under 35 U.S.C. 154(b) by 75 days.

(21) Appl. No.: 13/808,739

(22) PCT Filed: Jul. 8, 2011

(86) PCT No.: PCT/EP2011/061633
§ 371 (c)(1),
(2), (4) Date: Jan. 7, 2013

(87) PCT Pub. No.: WO2012/004388
PCT Pub. Date: Jan. 12, 2012

(65) Prior Publication Data
US 2013/0107275 A1 May 2, 2013

Related U.S. Application Data

(60) Provisional application No. 61/362,578, filed on Jul. 8, 2010.

(30) Foreign Application Priority Data

Sep. 13, 2010 (FR) .................................. 10 57268

(51) Int. Cl.
*G01B 11/02* (2006.01)
*G01B 9/02* (2006.01)
(Continued)

(52) U.S. Cl.
CPC .......... *G01B 9/02091* (2013.01); *A61B 5/0066* (2013.01); *G01B 9/02048* (2013.01);
(Continued)

(58) Field of Classification Search
CPC .. G01B 9/02091; A61B 5/0066; A61B 3/102; G01J 3/0208

USPC .................................................. 356/479, 497
See application file for complete search history.

(56) References Cited

U.S. PATENT DOCUMENTS 5,459,564 A    10/1995  Chivers
7,768,651 B2 *  8/2010  Ueno ..................... A61B 3/102
                                                             356/497

(Continued)

FOREIGN PATENT DOCUMENTS

DE     19624167 A1    1/1997
EP      1892501 A2    2/2008

(Continued)

OTHER PUBLICATIONS

International Search Report issued in PCT/EP2011/061633 mailed Oct. 31, 2011 (3 pages).

(Continued)

*Primary Examiner* — Tarifur Chowdhury
*Assistant Examiner* — Jonathon Cook
(74) *Attorney, Agent, or Firm* — Osha Liang LLP

(57) ABSTRACT

A device for three-dimensional imaging by full-field interferential microscopy of a volumic and scattering sample includes an imaging interferometer of variable magnification, allowing for the acquisition of at least one first and one second interferometric images resulting from the interference of a reference wave obtained by reflection of the incident wave on a reference mirror and an object wave obtained by backscattering of the incident wave by a slice of the sample at a given depth of the sample. The invention also relates to a processing unit that processes the interferometric images, a unit for axially displacing the interferometer relative to the sample for the acquisition of tomographic images for slices at different depths of the sample, and a unit for varying the magnification of the imaging interferometer for the acquisition of interferometric images of a slice for different magnification values.

7 Claims, 4 Drawing Sheets

(51) Int. Cl.

| | | |
|---|---|---|
| *A61B 5/00* | (2006.01) | |
| *G01B 11/24* | (2006.01) | |
| *G01J 3/02* | (2006.01) | |
| *G01J 3/10* | (2006.01) | |
| *G01J 3/28* | (2006.01) | |
| *G01J 3/45* | (2006.01) | |
| *G02B 21/14* | (2006.01) | |

(52) U.S. Cl.
CPC ........ *G01B9/02057* (2013.01); *G01B 11/2441* (2013.01); *G01J 3/0208* (2013.01); *G01J 3/0237* (2013.01); *G01J 3/10* (2013.01); *G01J 3/2823* (2013.01); *G01J 3/45* (2013.01); *G02B 21/14* (2013.01); *A61B 2562/046* (2013.01)

(56) References Cited

U.S. PATENT DOCUMENTS

| | | | |
|---|---|---|---|
| 2004/0105100 A1 | 6/2004 | Shirley | |
| 2005/0225769 A1 | 10/2005 | Bankhead et al. | |
| 2008/0304144 A1* | 12/2008 | Reimer et al. | 359/377 |
| 2013/0148106 A1* | 6/2013 | Tearney et al. | 356/72 |

FOREIGN PATENT DOCUMENTS

| | | |
|---|---|---|
| EP | 1961374 A1 | 8/2008 |
| FR | 2 817 030 A1 | 5/2002 |
| WO | 2005/108915 A1 | 11/2005 |

OTHER PUBLICATIONS

Written Opinion issued in PCT/EP2011/061633 mailed Oct. 31, 2011 (5 pages).

Fujimoto, James G. et al.; "Optical biopsy and imaging using optical coherence tomography"; Nature Medicine, vol. 1, No. 9; Sep. 1995; pp. 970-972 (3 pages).

Dubois, Arnaud et al.; "High-resolution full-field optical coherence tomography with a Linnik microscope"; Applied Optics, vol. 41, No. 4; Feb. 1, 2002; pp. 805-812 (8 pages).

Karamata, B. et al.; "Multiple scattering in optical coherence tomography. II. Experimental and theoretical investigation of cross talk in wide-field optical coherence tomography"; J. Opt. Soc. Am. A, vol. 22, No. 7; Jul. 2005; pp. 1380-1388 (9 pages).

Office Action issued in corresponding European Application No. 11738662.3 dated Aug. 4, 2015 (6 pages).

* cited by examiner

METHOD AND DEVICE FOR HIGH RESOLUTION FULL FIELD INTERFERENCE MICROSCOPY

TECHNICAL FIELD OF THE INVENTION

The present invention relates to a method and a device for three-dimensional imaging by full-field interferential microscopy, notably for cellular imaging.

STATE OF THE ART

The optical microscopy technique based on the acquisition of images with a very low depth of field (of around 1 μm) called optical sectioning, is highly developed in biology and in the medical field, fields in which the strong scattering of the tissues being observed makes the use of conventional microscopy useless.

Among the techniques used for high-resolution 3D imaging (resolution of around 1 micron), laser scanning confocal microscopy, based on the selective illumination of a minimum volume in the object and the detection of the optical response originating only from this volume by geometrical discrimination, is widely used. The use of lenses with strong numerical aperture (numerical aperture typically between 0.8 and 1.4) makes it possible to obtain a low depth of field suitable for obtaining optical sections.

Optical Coherence Tomography, or OCT, is a relatively recent imaging technique dating from the beginning of the 1990s, which allows for in depth exploration of scattering media in a non-invasive manner by being based on the selection of the ballistic photons backscattered or reflected by the structures of the medium being observed (see for example J. G. Fujimoto et al., "Optical biopsy and imaging using optical coherence tomography", Nature med. 1, 970-972 (1995)). At the root of all optical coherence tomography devices there is an interferometer, allowing for the correlation of the wave returning from the observed medium with a reference wave. This interferometer is illuminated by a source with a broad spectrum, and consequently a low coherence length, necessary for the discrimination of the reflections or backscatterings at different depths in the medium being probed. Just as in confocal microscopy, an image is obtained by point-by-point scanning of the observed sample. Unlike confocal microscopy, this technique makes it possible to combine an optical section of small thickness (of around 5 to 15 μm) with a high detection sensitivity, allowing for an imaging at greater depths in the tissues. This is particularly visible in the case of spectral OCT, for example, for which the acquisition of the voxels along the optical axis is performed by a spectrometric discrimination. In practice, the simultaneous acquisition of the voxels along the optical axis requires a significant depth of field of the imaging optical channel, namely at least equal to the desired depth of imaging in the tissue. This constraint explains the use of beams with a very low numerical aperture, hence a lower transverse resolution compared to confocal microscopy which uses very wide aperture lenses, but also a limitation on the aberrations introduced by the tissues, and consequently a better penetration. This technique has proven particularly suitable and effective in biomedical imaging, notably in the field of eye examination, for which the in vivo retina sections are obtained routinely, and provide the doctor with a diagnostic aid for various ocular pathologies. For other tissues of the human body, which are more dense, and have large effective scattering cross-sections, it has proven more difficult to obtain in depth images of optical sections to a level of resolution of a cell.

Unlike the conventional OCT approach, in which a transverse scan of the incident beam on the sample allows for the reconstruction of the images in cross sections parallel to the optical axis, the so-called full-field OCT, or FF-OCT, technique uses matrix detectors of CCD or CMOS type to take images of very high resolution, called "en face" images (see, for example, A. Dubois et al., "High resolution full field optical coherence tomography with a Linnik microscope", Appl. Opt. 41, 805-812 (2002)). This imaging technique uses lenses with medium numerical aperture (of about 0.5) unlike the conventional OCT which uses low numerical apertures as explained previously, which makes it possible to achieve much better transverse resolutions—of about 1 μm compared to approximately 10 μm for conventional OCT. It therefore offers a very good trade-off between sensitivity and resolution. Moreover, this imaging technique does not require the control of a scanning system and the sources used (halogen lamp for example) are inexpensive compared to the femtosecond laser or superluminescent diode sources used in conventional OCT.

FIG. 1 shows a schematic diagram of a full-field interferential microscope using incoherent light for the imaging of a volumic and scattering sample 1. Such a microscope is for example described in the patent application FR 2817030. The device, referenced 10 in FIG. 1, hinges around an imaging interferometer 100 of given magnification, illuminated by a source 101 of low spatial and temporal coherence, for example a halogen lamp, and linked to a processing unit 106. The interferometer 100 comprises a beam splitter element 102, for example a non-polarizing beamsplitter cube, defining two arms. In the configuration of FIG. 1, each arm includes a microscope objective, respectively 103 and 104, these two objectives being identical. Such a device is called Linnik interferometer. In one of the arms, which will hereinafter be called reference arm, there is a planar surface 105 of uniform reflectivity, placed in the image focal plane of the microscope objective 104. In the other arm, which will hereinafter be called object arm, the sample 1 for which the three-dimensional mapping of the backscattering amplitude is to be reconstructed is positioned. At the output of this interferometer, a tube lens, for example an achromatic doublet of large focal length, typically 300 mm, is used to conjugate the image focal planes of the two lenses on a multichannel sensor 108, for example a CCD camera. To benefit from a diffraction-limited transverse resolution, the focal length of this tube lens is chosen so as not to undersample the Point Spread Function or PSF of the objectives. The magnification of the interferometer is defined in this configuration by the focal characteristics of the microscope objectives and the tube lens. Glass plates 109, 110 are provided on each of the arms to compensate for dispersion.

Since the light source 101 has a low temporal coherence length, interferences between the light reflected by the reference surface 105 and that backscattered by the sample 106 occur only when the optical paths in the two arms are equal, to within a tolerance which is the effective coherence length. There is therefore a virtual slice in the object, called coherence slice, for which the backscattering information is relative to the interference state perceived by the camera. The light backscattered on either side of this slice is not coherent with that reflected by the reference, so it contributes to an overall background in the signal. By modulating the relative path difference of the two arms of the interferometer, by an axial displacement of the reference surface 105 using, for example, a piezoelectric plate 111, only the interference state carrying the coherence slice information is modulated, the background remaining constant. A synchronization of this modulation with the camera acquisition makes it possible to record different interference states. A non-linear combination of the duly obtained interferometric images then makes it possible to demodulate the coherence slice information, and to discriminate the information from the ballistic photons backscattered only by this slice, from the information from those having undergone scattering elsewhere in the sample (see for example the article by A. Dubois mentioned previously).

Due to the random nature of the structures forming the biological tissues, it is possible to record only two interferometric images, by using a CCD or CMOS camera for example, the phase being shifted by π on the reference arm of the interferometer between the acquisition of the two interferometric images, and to calculate the tomographic image by calculating the normalized difference of the two interferometric images. Moreover, the use of a spatially incoherent source makes it possible to limit the crosstalk effects between the pixels as is, for example, described in Karamata et al., "Multiple Scattering in optical coherence tomography II Experimental and theoretical investigation of crosstalk in wide-field optical coherence tomography", J. Opt. Soc. Am. A/Vol. 22, No. 7 (2005). A full-field tomographic image can then be acquired in the volume of the sample, and a displacement of the latter relative to the coherence plane or of the device relative to the sample makes it possible to record the three-dimensional information. Reconstructions in all directions, or other volumic representations can then be produced.

Using full-field OCT microscopy, it is thus possible to achieve, with a light source with a spectral width of about 300 nm centered towards 750 nm for example, an anatomopathological spatial resolution corresponding to a cellular resolution (approximately 1 micron in all three dimensions) at a depth of up to 1 millimeter in living tissues. For this, objectives of medium aperture can be used (10× or 20× magnification with a numerical aperture of between 0.3 and 0.5). Advantageously, the objective 104 on the reference arm operates in immersion mode (generally in water, whose refraction index n is 1.33) with a suitable correction of the geometrical and chromatic aberrations.

However, when a three-dimensional examination of a biological tissue is required for a diagnosis for example, the quantity of data that has to be acquired becomes gigantic. Typically, to image a volume of a square centimeter by a thickness of around 1 millimeter and an axial and lateral resolution of 1 micron, some hundred billion ($10^{11}$) voxels have to be stored. A voxel here corresponds to the basic volume of the sample in which a planar incident wave is focused, and whose section is given by the diffraction spot of the microscope objective in the absence of aberrations and whose length is given by the coherence length of the source divided by twice the reactive index of the medium. In an FF-OCT system, the effective unitary field of view is defined by the combination of the field of view of the objective and the size of the imaging camera related to the imaging plane. Because of its rectangular geometry, the camera generally limits the effective field of view to an area slightly less than the field of view of the objective. For example, the effective field of view obtained with a ×10 immersion objective coupled to a megapixel camera is about 1 mm². To acquire a field of view of about 1 cm², use is generally made of a scanning of the sample with a pitch roughly corresponding to the effective unitary field of view of the system, followed by a combination of the tomographic images obtained—or "stitching"—so as to obtain the wide-field image. This method is commonly used in microscopy, generally by displacement of the sample by translation of its support, typically a motorized two-axis translation plate.

However, such a method is slow and even by using cameras with millions of pixels, recording such images may take several hours. This processing time is detrimental, both for in-vivo examination applications, for example in dermatology, and for ex-vivo examination applications, for example for the examination of a tumor. Moreover, the information storage capacity has to be extremely large.

The issue of improving the data acquisition time and of limiting the quantity of information to be stored therefore arises, as a corrolorary to the acceleration in the development of devices for very-high-resolution imaging in tissues, of which the FF-OCT technique is a perfect illustration. The present invention discloses in particular a full-field optical coherence tomography imaging method and a device for implementing the same which makes it possible to considerably reduce the acquisition and processing time in the analysis of large samples.

SUMMARY OF THE INVENTION

According to a first aspect, the invention relates to a device for three-dimensional imaging by full-field interferential microscopy of a volumic a scattering sample comprising:
  an emission source for emitting an incident wave with low temporal coherence,
  an imaging interferometer of variable magnification, comprising a reference arm comprising a reference mirror, an object arm for receiving the sample, means for varying the relative path difference between the object and reference arms, a multichannel acquisition device and an optical conjugation device with variable magnification for optically conjugating the sample and said multichannel device, the imaging interferometer allowing for the acquisition of at least one first and one second interferometric images resulting from the interference of a reference wave obtained by reflection of the incident wave on said reference mirror and an object wave obtained by backscattering of the incident wave by a slice of the sample at a given depth of the sample, the at least two interferometric images having a phase difference obtained by varying the relative path difference between the two object and reference arms,
  a processing unit for processing said interferometric images making it possible to obtain a tomographic image of said slice of the sample,
  means for axially displacing the interferometer relative to the sample allowing for the acquisition of tomographic images for slices at different depths of the sample,
  means for varying the magnification of the conjugation device of the imaging interferometer allowing for the acquisition of interferometric images of a slice of the sample for different magnification values.

Thanks to the duly disclosed device, the user has the possibility of acquiring tomographic images, that is to say slices in depth from the sample, that are both "large field" (of the order of 1 cm²), for the observation of the macroscopic structures of the biological tissues for example, and "small-field" images (of the order of 1 mm²) of high resolution for the observation of the microscopic structures at a cellular scale, and all in a way suited to a clinical context in terms of procedure time, typically less than a few minutes to obtain and store the images.

Advantageously, the optical conjugation device comprises a microscope objective with variable magnification and a beam splitter element, making it possible to form said object and reference arms, allowing for a fine control of the magnification with a single objective.

For example, the imaging interferometer is of Michelson or Mirau type.

According to a variant, the emission source is a source with variable spectral width, the processing unit making it possible to obtain tomographic images of slices of the sample of different thicknesses, the thickness of the slice being determined by the temporal coherence length of the source. This configuration makes it possible to adjust the three-dimensional magnification of the device by acting both on the transverse and axial magnification.

For example, the emission source comprises a plurality of LEDs whose luminous fluxes are combined in an optical fiber bundle to form a beam of substantially Gaussian spectral profile.

According to a second aspect, the invention relates to a method for three-dimensional imaging by full-field interferential microscopy of a volumic and scattering sample comprising:
- the emission of an incident wave with low temporal coherence to form a reference wave by reflection on a mirror of a reference arm of an imaging interferometer and an object wave by backscattering by a slice of the sample at a given depth, said sample being positioned on an object arm of the interferometer,
- the formation, using a multichannel acquisition device and an optical conjugation device with variable magnification for optically conjugating the sample and the acquisition device, of at least one first and one second interferometric image for a given magnification value, said images resulting from the interference of the reference wave and the object wave, the at least two interferometric images having a phase difference obtained by varying the relative path difference between the object and reference arms,
- the processing of the interferometric images to obtain a tomographic image of the slice of the sample at said magnification value,
- the axial displacement of the interferometer relative to the sample for the acquisition of tomographic images of slices at different depths of the sample,
- the variation of the magnification of the optical conjugation device and the acquisition of interferometric images for one or more other magnification values,
- the processing of said new interferometric images to obtain tomographic images of at least one of said slices of the sample at a given depth, at said other magnification values.

According to a variant, the method also comprises the variation of the spectral width of the incident wave and the acquisition of interferometric images for one or more other values of the spectral width and the processing of said new interferometric images to obtain tomographic images of slices of the sample of different thicknesses, the thickness of the slice being determined by the temporal coherence length of the source.

Advantageously, a value of the spectral width of the incident wave is associated with a value of the magnification of the optical conjugation device to form a three-dimensional magnification value, the method then comprising the acquisition of large-field tomographic images of slices of the sample at a first three-dimensional magnification value, the identification of an area of interest of the sample, the acquisition of small-field tomographic images of slices of the sample at a second three-dimensional magnification value greater than the first three-dimensional magnification value.

BRIEF DESCRIPTION OF THE DRAWINGS

Other advantages and characteristics of the invention will become apparent from reading the description, illustrated by the following figures.

DETAILED DESCRIPTION

Figure 2:
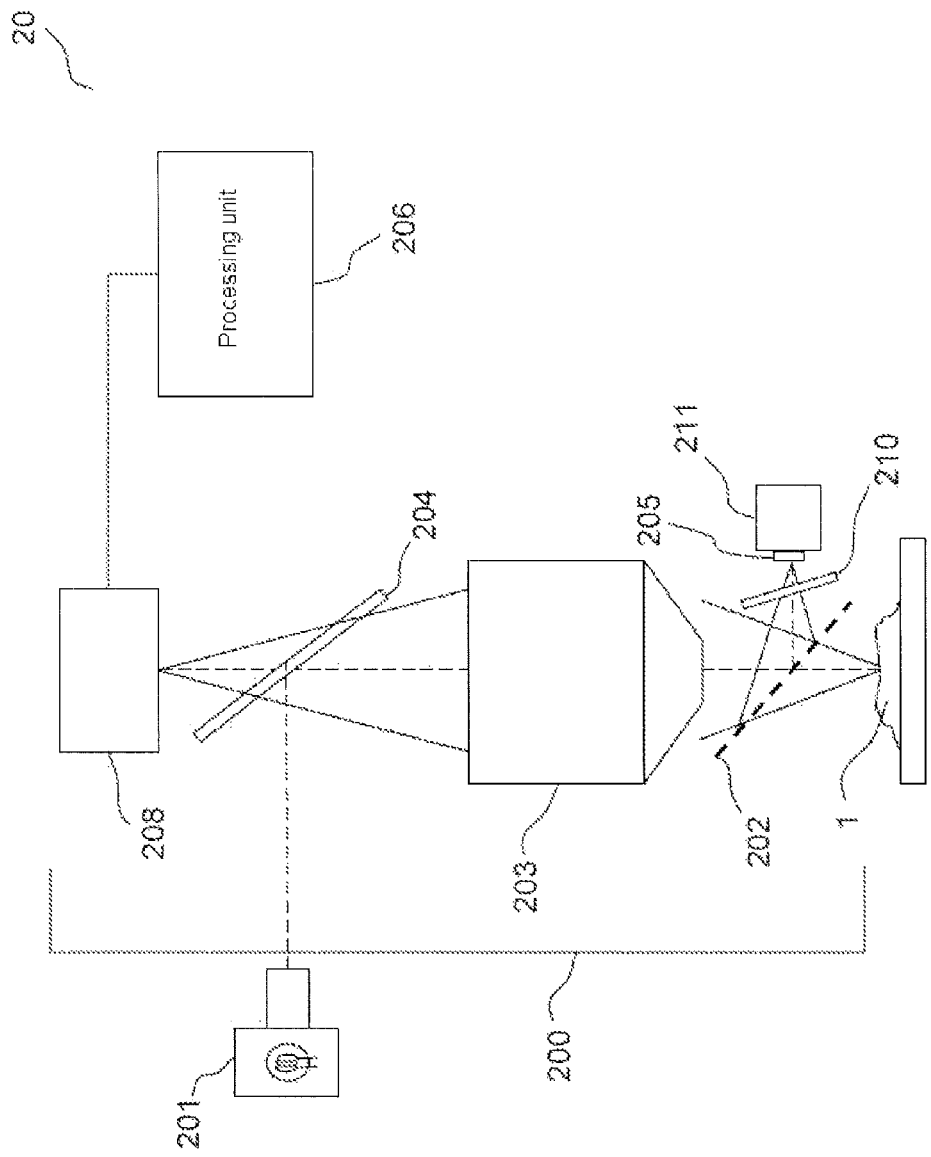
FIG. 2, an exemplary embodiment of a full-field interferential microscope for implementing the method according to the invention.

FIG. 2 represents a device 20 for three-dimensional imaging of a volumic and scattering sample 1 according to an exemplary embodiment of the invention. The sample is, for example, a biological tissue. It generally comprises an imaging interferometer 200 with variable magnification and a processing unit 206. In this example, the imaging interferometer has a Michelson-type configuration. It is illuminated by a source 201 with low spatial and temporal coherence, for example a halogen-type white-light source. The imaging interferometer 200 comprises a multichannel acquisition device 208, for example a CCD or CMOS camera, a first beam splitter element 204 that makes it possible to send into the interferometer the wave emitted by the source, a microscope objective 203, a second beam splitter element 202 for forming the two arms of the interferometers. The beam splitter element 202 is, for example, a pellicle beamsplitter in order to limit the geometric aberrations that may result from using beamsplitter cubes or plates when working at high numerical aperture and the stray reflections coming from the faces of such beamsplitter cubes or plates. The beam splitter element 202 defines, downstream of the microscope objective, a reference arm and an object arm on which the sample 1 is positioned. The reference arm includes a reflective mirror 205, with a reflection coefficient substantially equal to that of a biological tissue, typically a few percent (2 to 4% depending on the type of tissue), so as to optimize the contrast of the interferometric signal, and a translation stage 211 allowing for an axial displacement of the mirror, for example a piezoelectric-type translation stage to provide the modulation of the reference optical path. Advantageously, the interferometer also includes a compensation plate 210, tilted and made of a suitable material for compensating the dispersion induced by the sample in depth. This plate may be electrically controlled in rotation, the optimization criterion being the tomographic contrast of the image acquired. The acquisition in depth in the sample is produced either by an axial displacement of the sample relative to the imaging interferometer 200, or by a displacement of the imaging interferometer 200 relative to the sample, for example using a motorized translation stage fastened to the imaging interferometer 200. The microscope objective 203 is, according to a variant, a zoom objective—therefore an objective with variable magnification—whose imaging characteristics are compatible with the constraints of the FF-OCT tomography technique. In particular, it is not desirable to use excessively high numerical apertures, which results in aberrations linked to the light crossing the tissues being examined. Furthermore, achromaticity is desirable in the typical spectral range of tomography techniques in tissues, more precisely in the near infrared, for example between 600 and 900 nm. Finally, the working distance of the objective should preferably be constant during the variation of magnification of the objective, so as not to require any adjustment of the focus for each magnification value. In this exemplary embodiment, the microscope objective 203 is, for example, a zoom having a variation of magnification of about 10 to 20. This allows for a variation of resolution of approximately 1 µm to 20 µm, and a variation of field of approximately 0.5 mm$^2$ to 60 mm$^2$. For example, a suitable objective is the Zoom 160 model from Qioptiq Optem. It should be noted that other zoom objectives, for example from the same manufacturer, do exist and allow different operating ranges to be defined according to the type of sample studied. For example, a zoom having a variation of magnification of 7 makes it possible, for the corresponding model from the same manufacturer (Zoom 70XL model) to work on much greater fields but by sacrificing the maximum resolution obtained at the greatest magnification (from approximately 4 µm in the present case). These commercial objectives include a motor drive for varying the magnification, making it possible to control the imaged field by software, and possibly for the acquisition procedure to be automated according to predetermined magnification values. The configuration illustrated in FIG. 2 makes it possible to obtain an imaging interferometer with variable magnification with a single microscope objective, which is in particular advantageous in terms of cost. Alternatively, a lens turret with objectives of different magnifications could be used, but this would lead to an increase in the cost, mechanical complexity and bulk and a reduction in the mechanical precision due to the objective changes.

The interferometric imager 200 as is represented in FIG. 2 thus makes it possible to vary the magnification and therefore the field of observation and the lateral resolution of the interferometer. Thus, it will be possible for a user to image the area of interest for example with a first low magnification value and therefore a large field and a low lateral resolution (for example a square field of view of a few millimeters on each side and approximately 10 µm lateral resolution), then to increase the magnification and therefore work with a smaller field of view and better lateral resolution (typically a square field of view of a fraction of a millimeter on each side and a micron of lateral resolution), while retaining a limited number of pixels at the level of the detector (typically 1 megapixel or 1000×1000 pixels). This is particularly advantageous for the observation of biological tissues having structures of various sizes, as described previously.

In terms of acquisition time, the image of a square field of view for example of 5 mm side is thus produced using the device according to the invention with a minimum gain by a factor of 25 on the acquisition time of the large field which would be obtained with a combination of 5×5 images of smaller fields (1 mm side) by stitching, to which has to be added the displacement time of the sample according to a sequential geometry covering the total field, as well as the calculation time for the recombined image. This gain is obtained to the detriment of the resolution of the large-field image. However, it is observed that the analysis of these large-field images does not require, for the practitioner, the micron resolution obtained with maximum magnification. The large-field image makes it possible to visualize the macroscopic tissue structures such as the membranes, vessels, grouping of cells, and to locate the microscopic areas of interest, for which a cellular resolution is desirable. The device shown in FIG. 2 also makes it possible to optimize the quantity of useful data stored, since, in the case of large-field images recombined by stitching, approximately 90% of the pixels of the reconstructed image provide no additional information to the user.

The applicant has thus shown that with an imaging interferometer with variable magnification, it would be possible to considerably reduce the imaging time of a sample, and limit the quantity of data stored.

The scanning image devices, of which the conventional OCT is a relevant illustration in the present case, intrinsically offer the possibility of varying the amplitude of the transverse scanning to change the size of the field imaged. However, for this technique, the transverse resolution remains unchanged and the variation of the scanning amplitude does not allow for a significant gain in acquisition rate. The particular feature of the FF-OCT technique is that it is a full-field acquisition tomographic technique based on the acquisition of a plane of coherence without scanning by using a multichannel detector of CCD or CMOS camera type. Unlike the other acquisition tomographic techniques, the size variation of the acquired field of view is obtained here by a modification of the geometrical properties of the optical device for forming the image of the coherence slice on the detector, and leads to a beneficial variation of the transverse resolution of the image.

Figure 1:
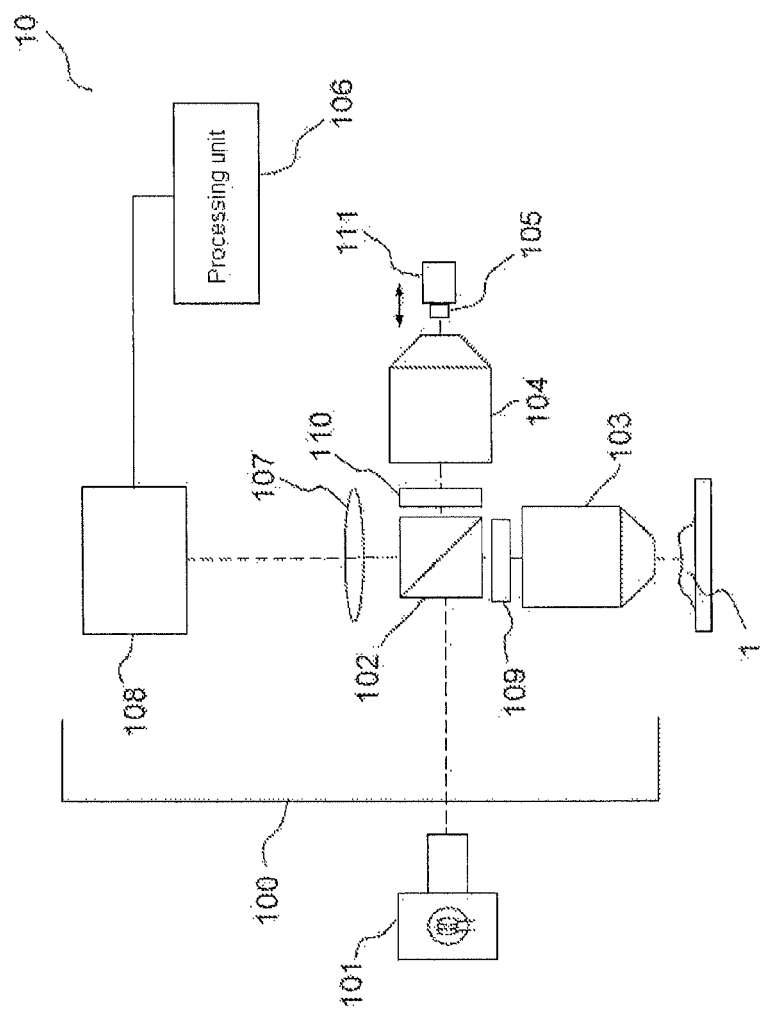
FIG. 1 (already described), a schematic diagram of a full-field interferential microscope in weakly coherent light according to the prior art.

One solution could involve using an optical system with variable magnification at the level of the tube lens 107 of the device shown in FIG. 1. Such a configuration would make it possible to vary the size of the field acquired advantageously for a Linnik-type device (FIG. 1) since it would require only a single optical system with variable magnification, without the need to incorporate the same system in each arm of the Linnink interferometer. However, such a device would not make it possible to address all the above mentioned constraints, since again, the optical resolution at the level of the sample would not vary, since it is linked to the lens used. Because of this, to retain a microscopic resolution, such a system would cause the use of multiple-megapixel cameras, which are slow and require the storage of large quantities of data.

Figure 3:
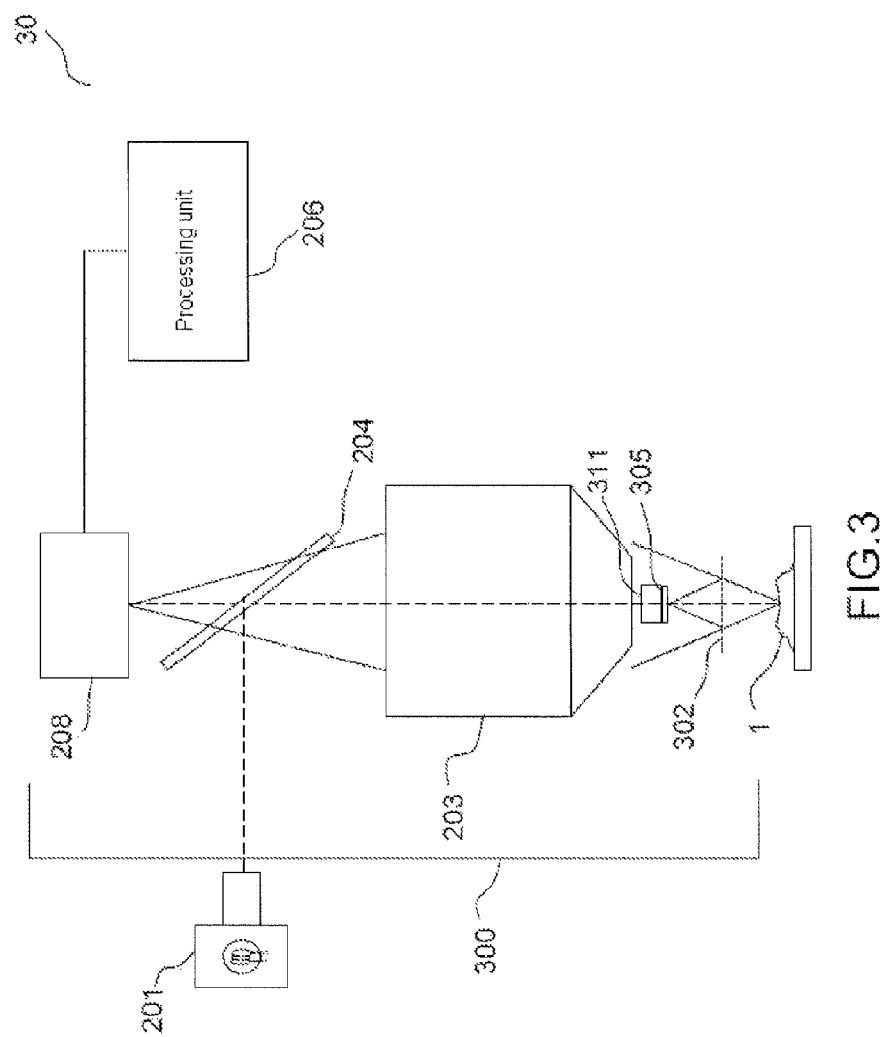
FIG. 3, another exemplary embodiment of a full-field interferential microscope for implementing the method according to the invention.

FIG. 3 shows a device 30 for three-dimensional imaging of a volumic and scattering sample 1, according to another example of the invention. In this example, the imaging interferometer 300 is of Mirau type. It is substantially the same as the imaging interferometer 200 of FIG. 2, except for the interferometer part situated in the object space of the variable magnification objective 203. The latter includes a beam splitter element 302 defining the two arms of the interferometer and positioned perpendicularly to the optical axis defined by the lens 203. The object arm collects the light from the sample 1, and the reference arm, including a reflection mirror 305 with properties equivalent to the mirror 205 of the interferometer 200, and a stage 311, typically a piezoelectric element, makes it possible to provide the modulation of the reference path. Alternatively, the modulation of the reference path could be obtained by moving the whole Mirau interferometric objective, defined by the objective 203, the reflection mirror 305 and the beam splitter element 302, for example using a translation stage, such as a piezoelectric focus scanner (e.g. PI PIFOC®). Advantageously, the splitter element 302 is a pellicle beamsplitter making it possible to avoid the geometrical aberrations and dispersion effects produced by beamsplitters such as tilted plates or beamsplitter cubes. Alternatively, a beamsplitter plate or beamsplitter cube can be used through a balancing of the two object and reference channels, both balancing of the geometrical aberrations and balancing of the dispersion. For example, a plate window can be introduced between the reflection mirror 305 and the splitter element 302, the characteristics of the plate being the same as those of the beam splitter element 302—except for the transmission coefficient—namely notably the thickness, the material used, the optical surface quality. In the device of FIG. 3, the other elements, namely the light source 201, the beam splitter element 204, the multichannel device 208, the processing unit 206, may be equivalent to those described in relation to the device 20 of FIG. 2.

According to a variant, the source 201 of the three-dimensional imaging device according to the invention has a variable spectral bandwidth making it possible to control the temporal coherence length of the incident wave and therefore the thickness of the analysis slice of the sample (or optical section), directly linked to this value. This control allows for a control of the axial resolution of the three-dimensional imaging, also called "spectral zoom". In practice, as has previously been described, the spectral bandwidth of the source in OCT imaging defines the axial resolution—or the thickness of the optical section—of the three-dimensional image that is to be formed. The axial resolution is proportional to the square of the average wavelength of the spectrum by the width of the effective spectrum, the effective spectrum being defined by the product of the spectrum of the source by the spectral response of the acquisition device, for example the camera. Thus, a modification of the spectral width results in a variation of the axial resolution, thus making it possible to produce a spectral zoom. The use of a source with a large spectrum, whose width can be controlled, makes it possible to adapt the axial resolution according to structures that are to be imaged and to the optical field of interest. For example, the spectral bandwidth is initially reduced to form a thick slice or optical section, typically around 10 microns, and work with a fast acquisition time due to the reduced number of planes to be explored in the depth of the sample and the increase in the backscattering level. This step is advantageously associated with a step for acquisition of the interferometric images with a low transverse resolution (low magnification), allowing for the acquisition of a rapid 3D image, with low resolution, to very rapidly give the user an image of the whole sample. When the user has identified an area of interest, increasing the spectral bandwidth makes it possible to increase the axial resolution and see more details in the thickness of the sample. The combined use of the objective with variable magnification and the spectral zoom then makes it possible to have access to a high-resolution 3D image.

An incoherent source with variable spectral bandwidth can, for example, be produced by combining, in a bundle of optical fibers, the light fluxes from light-emitting diodes (LED) having different emission wavelengths, distributed substantially uniformly along the desired spectral bandwidth. The selection of the spectral bandwidth and of the spectral profile of the duly constructed source can then be done by adjusting the output optical power of each LED individually, for example by controlling the intensity supply of each LED. It is generally preferable to have an emission source with Gaussian spectral profile to avoid echoes in tomographic images. Indeed, the axial profile of the coherence zone making it possible to isolate the coherent photons is directly proportional to the Fourier transform of the emission spectrum of the incoherent source. If this spectrum is not a Gaussian, its Fourier transform exhibits lateral rebounds, and there are then secondary areas of coherence on either side of the coherence plane, possibly generating a stray tomographic signal. The applicant has shown that a minimal spectral separation of the emission spikes of each LED associated with a suitable choice of the number of LEDs and of the output powers would make it possible to obtain an acceptable Gaussian profile.

Figure 4:
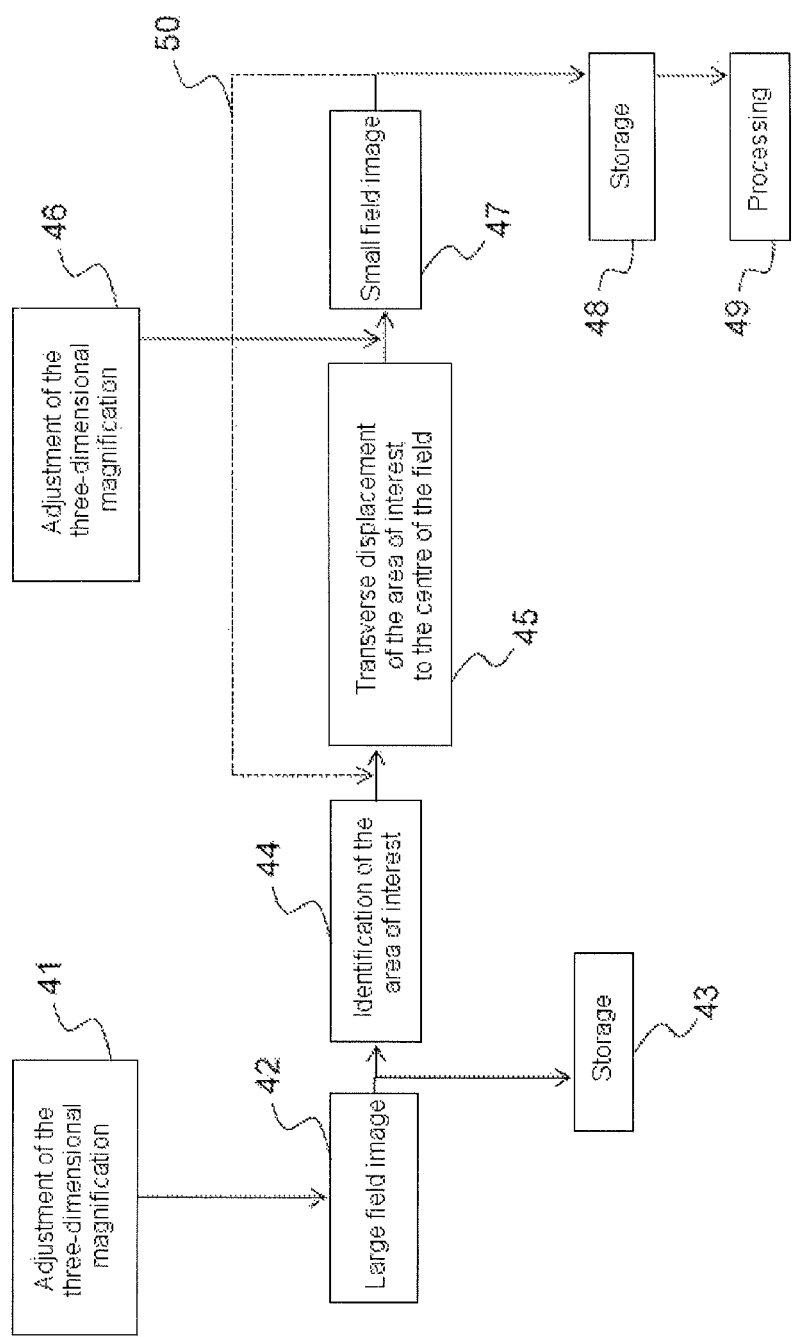
FIG. 4, a block diagram of the steps of an exemplary imaging method according to the invention.

FIG. 4 shows a block diagram of the three-dimensional imaging method according to the invention. A first adjustment of the three-dimensional magnification of the objective is made at the start of the procedure (41), so as to obtain a large-field image. The adjustment of the magnification includes the adjustment of the transverse magnification, using, for example, the variable magnification objective, and possibly the adjustment of the axial magnification when the device is equipped with a source with variable spectral bandwidth. It is then possible, once the sample is arranged in front of the imaging interferometer at the working distance of the objective, to acquire and visualize, using a processing and display unit such as, for example, a computer, a three-dimensional tomographic image of the largest possible area (step 42), this image typically having a surface area of around 1 cm². An exploration in depth can be performed by axial displacement of the sample relative to the imaging interferometer, so as to select the desired imaging depth, or else to define the limits in depth of the volume acquired. This order of magnitude of surface area, associated with the resolution given by the objective for the lowest magnification, makes it possible, on most biological samples, to visualize the macroscopic structures of the tissues, such as, for example, the vessels, fibers, grouping of cells, cancerous regions or other pathological regions. A first adjustment of the thickness of the optical section can be made, so as to select a preferentially large thickness, of the order of 10 µm, which makes it possible to define and explore a volume more rapidly by reducing the number of imaging planes needed. This adjustment can be made by adjusting the width of the illumination spectrum as described previously. This first three-dimensional image is stored, for example, in a digital form (step 43). This first type of image enables the user to identify one or more small areas of interest, and the associated depth, on which he wants to have microscopic information, namely an image at the cellular scale, requiring a high resolution, typically 1 to a few micrometers (step 44). The sample is then displaced so as to bring an area of interest to the centre of the imaging field defined by the interferometer (step 45). A second adjustment (step 46) of the same parameters is made, namely an adjustment of the magnification of the objective making it possible to define a smaller imaging field and a greater resolution, and an adjustment of the thickness of the optical section making it possible to obtain a better axial resolution. This adjustment makes it possible to define a second imaging volume with a cellular resolution, that is to say of the order of 1 µm in all three dimensions (step 47). This second three-dimensional image is acquired and stored (step 48), for example in digital form. This stored image is then available for any image-processing operations (step 49). This second type of acquisition can be repeated for other areas of the sample for which a cellular resolution is required (step 50).

The method described in this way for the in depth imaging of a sample makes it possible to reduce the recording time of the final useful image. In practice, whether it is a large-field image with low resolution or a small-field image with high resolution, all the pixels are useful, unlike in the method usually applied in which 90% of the high-resolution image is not useful to the user. It is thus possible to also optimize the storage capabilities of the three-dimensional imaging system.

Another advantage of the duly described method is that, due to the reduced acquisition time, it is possible to visualize full-field images at a reasonable rate, typically a few Hz, which is not possible when the field has to be scanned and the images obtained have to be recombined. This represents a significant ease of use for the practitioner, because the imaging in depth in real time of volumic samples makes it possible to identify the main areas of interest without having to use lengthy and systematic procedures for the whole sample before having access to the area of interest.

Although described through a number of detailed exemplary embodiments, the method and the device for three-dimensional imaging by full-field interferential microscopy according to the invention include different variants, modifications and refinements which will obviously become apparent to those skilled in the art, it being understood that these different variants, modifications and refinements fall within the scope of the invention as defined by the following claims.

The invention claimed is:

1. A device for three-dimensional in depth imaging by full-field interferential microscopy of a volumic and scattering sample, the device comprising:
   an emission source with low temporal coherence,
   wherein the emission source has a variable spectral bandwidth;
   an imaging interferometer of variable magnification, comprising:
      a reference arm comprising a reference mirror,
      an object arm for receiving the scattering sample,
      means for varying the relative path difference between the object and reference arms,
      a multichannel acquisition device and an optical conjugation device with variable magnification for optically conjugating the sample and said multichannel acquisition device,
      wherein the imaging interferometer allows for the acquisition of at least one first and one second interferometric images resulting from the interference of a reference wave obtained by reflection of light emitted by the emission source on said reference mirror and an object wave obtained by backscattering of light emitted by the emission source by a slice of the sample at a given depth into the sample, the at least two interferometric images having a phase difference obtained by varying the relative path difference between the object and reference arms;
   a processing unit for processing said interferometric images making it possible to obtain a tomographic image of said slice of the sample;
   means for axially displacing the interferometer relative to the sample allowing for the acquisition of tomographic images for slices at different depths into the sample;
   means for varying the magnification of the conjugation device of the imaging interferometer allowing for the acquisition of interferometric images of a slice of the sample for different magnification values; and
   means for varying the spectral bandwidth of the emission source allowing for the acquisition of interferometric images of slices of the sample of different thicknesses.

2. The three-dimensional imaging device as claimed in claim 1, wherein the optical conjugation device comprises a microscope objective with variable magnification and a beam splitter element, allowing the forming of said object and reference arms.

3. The three-dimensional imaging device as claimed in claim 2, wherein the imaging interferometer is of Michelson or Mirau type.

4. The three-dimensional imaging device as claimed in claim 1, wherein the emission source comprises a plurality of LEDs whose luminous fluxes are combined in an optical fiber bundle to generate a beam of substantially Gaussian spectral profile.

5. A method for three-dimensional in depth imaging by full-field interferential microscopy of a volumic and scattering sample comprising:
   emission of light by an emission source with low temporal coherence to form a reference wave by reflection on a mirror of a reference arm of an imaging interferometer and an object wave by backscattering by a slice of the sample at a given depth into the sample, said scattering sample being positioned on an object arm of the interferometer, wherein the emission source has a variable spectral bandwidth;
   formation, using a multichannel acquisition device and an optical conjugation device with variable magnification for optically conjugating the sample and the acquisition device, of at least one first and one second interferometric image for a given magnification value, said images resulting from the interference of the reference wave and the object wave, the at least two interferometric images having a phase difference obtained by varying the relative path difference between the object and reference arms;
   processing of the interferometric images to obtain a tomographic image of the slice of the sample at said magnification value;
   axial displacement of the interferometer relative to the sample for the acquisition of tomographic images of slices at different depths into the sample;
   variation of the magnification of the optical conjugation device and acquisition of interferometric images for one or more other magnification values;
   processing of said new interferometric images to obtain tomographic images of at least one of said slices of the sample at a given depth, at said other magnification values;
   variation of the spectral bandwidth of the emission source and acquisition of interferometric images for one or more other values of the spectral bandwidth; and
   processing of said new interferometric images to calculate tomographic images of slices of the sample of different thicknesses, the thickness of the slice being determined by the spectral bandwidth of the emission source.

6. The three-dimensional imaging method as claimed in claim 5, wherein:
   a value of the spectral width of the incident wave is associated with a value of the magnification of the optical conjugation device to form a three-dimensional magnification value,
   the method further comprising:
      acquisition of large-field tomographic images of slices of the sample at a first three-dimensional magnification value;
      identification of an area of interest of the sample; and
      acquisition of small-field tomographic images of slices of the sample at a second three-dimensional magnification value, greater than the first three-dimensional magnification value.

7. A device for three-dimensional in depth imaging by full-field interferential microscopy of a volumic and scattering sample, the device comprising:
   an emission source with low temporal coherence, wherein the emission source has a variable spectral bandwidth;
   an imaging interferometer of variable magnification, comprising:
      a reference arm comprising a reference mirror,
      an object arm for receiving the scattering sample,
      means for varying the relative path difference between the object and reference arms, a multichannel acquisition device and an optical conjugation device with variable magnification for optically conjugating the sample and said multichannel acquisition device, wherein the imaging interferometer acquires at least one first and one second interferometric images resulting from the interference of a reference wave obtained by reflection of light emitted by the emission source on said reference mirror and an object wave obtained by backscattering of light emitted by the emission source by a slice of the sample at a given depth into the sample, the at least two interferometric images having a phase difference obtained by varying the relative path difference between the object and reference arms;

a processing unit for processing said interferometric images making it possible to obtain a tomographic image of said slice of the sample;

means for axially displacing the interferometer relative to the sample allowing for the acquisition of tomographic images for slices at different depths into the sample;

means for varying the magnification of the conjugation device of the imaging interferometer allowing for the acquisition of interferometric images of a slice of the sample for different magnification values; and means for varying the spectral bandwidth of the emission source allowing for the acquisition of interferometric images of slices of the sample of different thicknesses.

* * * * *